United States Patent
Eggersmann

(10) Patent No.: US 9,234,215 B2
(45) Date of Patent: Jan. 12, 2016

(54) METHOD AND DEVICE FOR OPERATING A FERMENTATION PLANT

(75) Inventor: Karlgünter Eggersmann, Marienfeld (DE)

(73) Assignee: ZEROWASTE ENERGY, LLC, Layfayette, CA (US)

( * ) Notice: Subject to any disclaimer, the term of this patent is extended or adjusted under 35 U.S.C. 154(b) by 465 days.

(21) Appl. No.: 12/948,147

(22) Filed: Nov. 17, 2010

(65) Prior Publication Data

US 2012/0122175 A1  May 17, 2012

(51) Int. Cl.
*C12P 5/02* (2006.01)
*C12M 1/107* (2006.01)
*C12M 1/00* (2006.01)

(52) U.S. Cl.
CPC ............... *C12P 5/023* (2013.01); *C12M 21/04* (2013.01); *C12M 47/18* (2013.01); *Y02E 50/343* (2013.01)

(58) Field of Classification Search
None
See application file for complete search history.

(56) References Cited

U.S. PATENT DOCUMENTS

2008/0299634 A1* 12/2008 Lutz .............................. 435/167

FOREIGN PATENT DOCUMENTS

| EP | 1428868 | 6/2004 |
|---|---|---|
| EP | 1736535 | 12/2006 |
| EP | 1811015 | 7/2007 |
| EP | 1997875 | 12/2008 |
| WO | WO 0206439 | 1/2002 |
| WO | WO 2005054423 | 6/2005 |

OTHER PUBLICATIONS

European Search Report in Application EP09 00 6326, EPO, Oct. 29, 2009.

* cited by examiner

*Primary Examiner* — Robert Yamasaki
(74) *Attorney, Agent, or Firm* — Bourque and Associates, PA

(57) ABSTRACT

A method for operating a fermentation plant with at least one digester (1) that is supplied with a substrate (1*a*). The substrate (1*a*) is percolated using a percolate (2*a*) from a percolate container (2) and biogas that is generated via the percolation process in the digester (1) or/and in the percolate container (2) is drawn off. The drawn off biogas is treated in a biogas treatment device (3) and the $CO_2$-containing exhaust gas that is generated during the treatment is introduced into the digester (1) using a purge line (4), for forcing out and drawing off the biogas that was generated in the digester (1). Alternatively $CO_2$-containing biogas that was generated in an additional digester (1) in a different fermentation process can be introduced into the digester (1) using a purge line (4) for forcing out and drawing off the biogas that was generated in the digester (1). The $CO_2$-containing purge gas is supplied to the digester (1) such that the $CO_2$-containing purge gas is forced to pass through the substrate (1*a*) dislodging any trapped biogas.

5 Claims, 1 Drawing Sheet

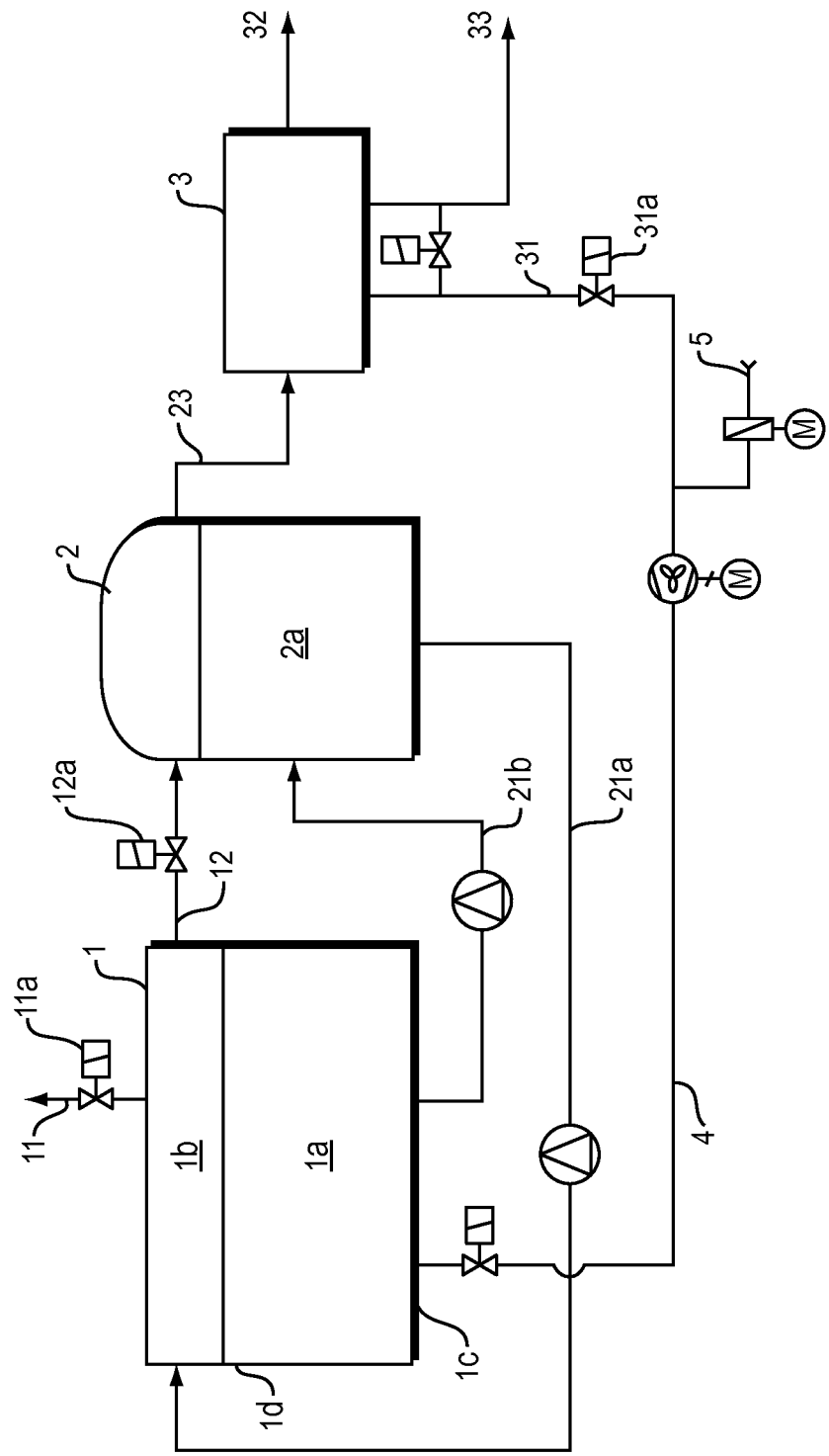

METHOD AND DEVICE FOR OPERATING A FERMENTATION PLANT

TECHNICAL FIELD

The invention relates to a method for operating a fermentation plant and more particularly, to a method and device that separates biogas from $CO_2$ gas and returns the $CO_2$ gas to the digester of the fermentation plant, forcing the $CO_2$ gas to pass through the substrate in the digester to force out and recover any trapped biogas located in the substrate.

BACKGROUND INFORMATION

In typical fermentation methods, a percolate flows through a substrate in a fermentation digester and is collected primarily at the bottom of the digester, returned to a percolate container and from there can be fed to the digester again. This creates methane-containing biogas in the digester and also in the percolate container, said biogas being discharged from the digester and/or the percolate container and fed to a biogas treatment system to increase the methane concentration. With biogas treatment, the biogas to be obtained is separated from other undesired components and is supplied for further use. Among other things, the treatment produces a significant amount of $CO_2$ gas.

To supply the biogas at the end of the process from the digester to the biogas treatment system, the biogas-containing volume above the substrate must be purged after the fermentation process using purge gas in order to eliminate the biogas from the volume. EP 1 997 875 A1 discloses the use of $CO_2$-containing gas from the treatment system for this purpose.

The fermentation process also generates a considerable amount of biogas, which is, however, "trapped" in the substrate itself. This is released during substance handling or reprocessing of the digistate. Thus, the released biogas portions, in particular methane, are not recovered and enter uncontrolled into the atmosphere.

SUMMARY

It is, therefore, one object of the invention to provide a method that does not have the aforementioned disadvantages and that reduces the methane loss to a minimum.

The present invention features a method for operating a fermentation plant with at least one digester (1) to which a substrate to be digested (1a) is supplied, whereby the substrate (1a) is percolated with a percolate (2a) from a percolate container (2), and biogas that is generated in the digester (1) or/and in the percolate container (2) is withdrawn, whereby the withdrawn biogas is treated in a biogas treatment device (3) and wherein $CO_2$-containing exhaust gas that is generated during treatment in the treatment device (3) is introduced into the digester (1) using a purge line (4) for removing any biogas that was generated in the digester (1), whereby the $CO_2$-containing purge gas is introduced into the digester (1) such that it passes through the substrate (1a). In one embodiment, the $CO_2$-containing purge gas is introduced into the substrate (1a) such that any gas that is present in the substrate (1a) is dislodged into the substrate-free volume (1b) of the digester (1). The $CO_2$-containing purge gas may be introduced into a bottom region of the digester (1) and in addition, such that the $CO_2$-containing purge gas passes through the substrate (1a) essentially uniformly from bottom to top.

After purging with the $CO_2$-containing purge gas, the present method may also provide fresh air that is introduced into the digester (1) via the purge line (4). During the supply of the $CO_2$-containing purge gas, the biogas is withdrawn via a withdrawal line (12, 23). After the conclusion of the purging process with $CO_2$-containing gas, a biogas withdrawal port is closed and a venting line (11) is opened.

The present invention also discloses and features a device for carrying out the method as set forth above. The device includes at least one digester (1) for supplying a substrate (1a), a percolate container (2) that is connected to a digester (1) via a percolate return line (21b) and a percolate supply line (21a) for receiving percolate (2a), at least one biogas withdrawal line (12, 23) for removing biogas that has been generated in the digester (1), with a purge line (4) for introducing purge gas into the digester (1), whereby a treatment device (23) for treating biogas and/or at least one additional digester (1) is provided, whereby the treatment device (3) for the purpose of supplying $CO_2$-containing exhaust gas generated during the treatment process via an exhaust gas line (31) and/or the additional digester (1) for supplying the $CO_2$-containing biogas that was generated during the fermentation process in the additional digester (1) can be connected with the purge line (4), whereby a port on the digester (1) for the purge line (4) is arranged such that during the purging process, $CO_2$-containing gas flows through the substrate that is located in the digester (1).

Accordingly, utilizing the method according to the invention, the $CO_2$-containing purge gas passes through the substrate. Preferably, the purge gas is supplied to the digester over a large area at the bottom of the digester. In this manner, the substrate is purged and any trapped biogas contained therein is forced into the volume above the substrate and can be removed to the biogas treatment system in a known manner. The $CO_2$-containing purge gas can be obtained as exhaust gas from the biogas treatment system or alternatively and/or as a supplement, it is also possible to supply $CO_2$-containing biogas that was generated in a different digester or by a different fermentation process in an earlier phase of the digestion process to the digester that is to be purged.

BRIEF DESCRIPTION OF THE DRAWINGS

These and other features and advantages of the present invention will be better understood by reading the following detailed description, taken together with the drawings wherein:

FIG. 1 is block diagram of a representative system on which the method of the present invention can be practiced.

DETAILED DESCRIPTION OF THE PREFERRED EMBODIMENTS

A substrate 1a is supplied to a digester 1. Shown is only one digester but systems with numerous digesters are possible. The digester 1 is connected to a percolate container 2 via a supply line 21a that is used to feed percolate 2a into the digester 1. During the fermentation process, the percolate percolates through the substrate 1a. The percolate is collected in the lower region of the digester 1 and is returned to the percolate container 2 via a return line 21b.

Biogas is generated during the fermentation process and collects in the digester primarily in volume 1b above the substrate 1a. In addition, biogas is present in a trapped manner in the substrate 1a and cannot easily enter into the volume 1b. Furthermore, additional biogas is generated in percolate container 2. The biogas that is present in the regions 1b and 1a is removed by the purge process according to the invention. For this purpose, a biogas line 12 is provided between digester 1 and percolate container 2 and an additional line 23 between percolate container 2 and a treatment device 3. The $CO_2$-containing gas that is generated during the treatment process in the treatment device 3 is used for purging. Thus, $CO_2$-containing gas refers to a gas that contains predominantly $CO_2$. It may contain $CO_2$ exclusively but other components are conceivable.

The biogas treatment generates—in addition to highly concentrated methane, which is provided via line 32—predominantly $CO_2$-containing exhaust gas that can be removed via line 33 or can be introduced via line 31 into the purge line 4 that leads to the digester 1. The purge port at the digester 1 is positioned such that the purge gas that is introduced via purge line 4 passes through the substrate. Preferably, the port for the purge line 4 is provided at the bottom 1c or in the bottom area of the digester 1 or on the side in a region 1d of the digester 1 that is still covered by the substrate 1a. In addition, a distribution device (not shown) can be provided to guide the purge gas through the substrate at several locations. This can be accomplished in the digester 1 or through splitting the purge line 4 before the digester 1. In any case, several purge gas ports can be provided for introducing the purge gas into the substrate 1a of the digester 1.

The $CO_2$-containing purge gas is supplied under pressure to the digester 1 such that any biogas that is still trapped in the substrate 1a is dislodged from the substrate 1a. The port to the biogas line 12 or a corresponding valve 12a, respectively, is opened such the biogas that has been dislodged from the substrate 1a and the substrate-free volume 1b can be removed via the percolate container 2 and the line 23 to the treatment device 2. Once the biogas has been removed from the digester 1, or a specified switchover point is reached that can be, for example, tied to a threshold value of the biogas (generally methane gas) concentration, the valve 12a in line 12 can be closed again and the exhaust valve 11a to the exhaust line 11 can be opened; the valve 31a of the $CO_2$-line will be closed and the $CO_2$-supply will be stopped. Now an additional purge is carried out using fresh air that is provided to the purge line 4 via a fresh air line 5. The exhaust gas that escapes through the exhaust line 11 is subjected to an exhaust gas treatment and/or discharge that shall not be described in detail here.

In the shown processing variant, an exhaust gas from the biomethane treatment is used as the purge gas. Biogas that is generated in another digester (not shown) can be used in place of the exhaust gas. A large amount of $CO_2$ is generated in the biogas in the first phase of the fermentation process. This $CO_2$-containing biogas from a digester can be used for purging another digester, for example by connecting the purge gas port of the digester to be purged to the biogas line of another digester.

Using the method according to the invention, the methane gas loss can be reduced significantly by the method according to the invention. In addition, the efficiency of the biogas production can be increased because the biogas that is present in the substrate can be dislodged and supplied to the treatment system as well.

Modifications and substitutions by one of ordinary skill in the art are considered to be within the scope of the present invention, which is not to be limited except by the following claims.

The invention claimed is:

1. A method for operating a fermentation plant with at least one digester (1) into which a substrate to be digested (1a) is supplied, the method comprising:
   percolating the substrate (1a) with a percolate (2a) from a percolate container (2),
   withdrawing biogas, containing methane and $CO_2$, that is generated in the digester (1) or/and in the percolate container (2) during a fermentation period,
   treating the withdrawn methane and $CO_2$-containing biogas in a biogas treatment device (3) to separate predominantly $CO_2$-containing exhaust gas from said methane and $CO_2$-containing biogas, and
   introducing said predominantly $CO_2$-containing exhaust gas that is generated during treatment of the withdrawn biogas in the treatment device (3) into the digester (1) after the fermentation period, using a purge line (4), as $CO_2$-containing purge gas, wherein the $CO_2$-containing purge gas is introduced under pressure into a bottom region of the digester (1) and thus into a bottom region of the substrate (1a) through one or more purge ports such that any biogas that is present in the substrate (1a) is dislodged into the substrate-free volume (1b) of the digester (1) above the substrate (1a) for subsequent collection and removal.

2. The method as set forth in claim 1, characterized in that the $CO_2$-containing purge gas is distributed into the bottom of the digester (1) such that the $CO_2$-containing purge gas passes through the substrate (1a) essentially uniformly from bottom to top.

3. The method as set forth in claim 1, characterized in that after purging with the $CO_2$-containing purge gas, fresh air is introduced into the digester (1) via the purge line (4).

4. A method as set forth in claim 1, characterized in that during the supply of the $CO_2$-containing purge gas, the biogas is withdrawn via a withdrawal line (12, 23).

5. A method as set forth in claim 1, characterized in that after the conclusion of the purging process with $CO_2$-containing gas, a biogas withdrawal port is closed and a venting line (11) is opened.

* * * * *